United States Patent [19]

Cross et al.

[11] 4,363,912

[45] Dec. 14, 1982

[54] INDOLE THROMBOXANE SYNTHETASE INHIBITORS

[75] Inventors: Peter E. Cross, Canterbury; Roger P. Dickinson, Dover, both of England

[73] Assignee: Pfizer Inc., New York, N.Y.

[21] Appl. No.: 326,800

[22] Filed: Dec. 3, 1981

[30] Foreign Application Priority Data

Dec. 15, 1980 [GB] United Kingdom ............... 8040081

[51] Int. Cl.$^3$ ........................................ C07D 401/06
[52] U.S. Cl. ................................................ 546/273
[58] Field of Search ....................... 546/273; 424/263

[56] References Cited

U.S. PATENT DOCUMENTS 4,322,533 3/1982 Lesher et al. ...................... 424/263

FOREIGN PATENT DOCUMENTS 2045244 10/1980 United Kingdom .

OTHER PUBLICATIONS

Ciba Ltd., Chem. Abstracts, vol. 65, 12175h, (1966).
Eur. J. Med. Chem.-Chimica Therapeutica, May-Jun. 1975, vol. 10, No. 3, pp. 276-285-English Summary.

*Primary Examiner*—Henry R. Jiles
*Assistant Examiner*—Bernard Dentz
*Attorney, Agent, or Firm*—Charles J. Knuth; James H. Monroe

[57] ABSTRACT

A series of novel 3-(pyrid-3- or -4-ylalkyl)-indoles useful as inhibitors of the action of the thromboxane synthetase enzyme without significantly inhibiting the action of the prostacyclin synthetase or cyclo-oxygenase enzymes is disclosed.

7 Claims, No Drawings

INDOLE THROMBOXANE SYNTHETASE INHIBITORS

BACKGROUND OF THE INVENTION

Research work has established that in most tissues the major product of the arachiodonic acid metabolism is either of two unstable substances, thromboxane $A_2(TxA_2)$ or prostacyclin ($PGI_2$). (Proc. Nat. Acad. Sci. U.S.A., 1975, 72, 2294, Nature, 1976, 263, 663, Prostaglandins, 1976. 12, 897). In most cases the prostaglandins $PGE_2$, $PGF_2$ and $PGD_2$ are comparatively minor by-products in this biosynthetic pathway. The discovery of thromboxane $A_2$ and prostacyclin has significantly increased out understanding of vascular homeostasis, prostacyclin for instances is a powerful vasodilator and inhibitor of platelet aggregation, and in this last respect is the most potent endogenous substance so far discovered. The prostacyclin synthetase enzyme is located in the endothelial layer of the vasculature, and is fed by endoperoxides released by blood platelets coming into contact with the vessel wall. The prostacyclin thus produced is important for prevention of platelet deposition on vessel walls. (Prostaglandins, 1976, 12, 685, Science, 1976, 17, Nature, 1978, 273, 765).

Thromboxane $A_2$ is synthesised by the thromboxane synthetase enzyme which is located in, for example, the blood platelets. Thromboxane $A_2$ is a powerful vasoconstrictor and pro-aggregatory substance. As such its actions are in direct opposition to those of prostacyclin. If, for any reason, prostacyclin formation by the vasculature is impaired, then the endoperoxides produced by platelets coming into contact with the vessel wall are converted into thromboxane, but are not converted effectively into prostacyclin (Lancet, 1977, 18, Prostaglandins, 1978, 13, 3). Alteration of the prostacyclin/thromboxane balance in favour of the latter substance could result in platelet aggregation, vasospasm (Lancet, 1977, 479, Science, 1976, 1135, Amer. J. Cardiology, 1978, 41, 787) and an increased susceptibility to athero-thrombosis (Lancet (i) 1977, 1216). It is also known that in experimental atherosclerosis prostacyclin ganeration is suppressed and thromboxane $A_2$ production is enhanced (Prostaglandins, 1977, 14, 1025 and 1035). Thus thromboxane $A_2$ has been implicated as the causative agent in variant angina, myocardial infarction, sudden cardiac death and stroke (Thromb. Haemostasis, 1977, 38, 132). Studies in rabbits have shown that ECG changes typical of these conditions were produced when freshly prepared thromboxane $A_2$ was injected directly into the animal's heart (Biochem. aspects of Prostaglandins and Thromboxanes, Editors, N. Kharasch and J. Fried, Academic Press 1977 page 189). This technique is considered to represent a unique animal model of the heart attacks of coronary patients and has been used to show that administration of a compound believed to antagonise the effects of thromboxane $A_2$ protects the rabbits from the adverse consequences of thromboxane $A_2$ injection.

Another area where a $PGI_2/TxA_2$ imbalance is considered to be a contributory factor is that of migraine. The migraine headache is associated with changes in intra and extracerebral blood flow, in particular a preheadache reduction of cerebral blood flow followed by dilatation in both vascular areas during the headache phase.

Prior to the development of the headache, blood levels of 5-hydroxytryptamine are elevated, and this suggests the occurrence of in vivo aggregation and release of the amine from the platelet stores. It is known that the blood platelets of migraine patients are more prone to aggregate than are those of normal individuals (J. Clin. Pathol., 1971, 24, 250, J. Headache, 1977, 17, 101). Furthermore, it has now been postulated that not only is an abnormality of platelet function a major factor in the pathogenesis of migraine attacks but it is in fact their prime cause (Lancet (i), 1978, 501). Thus a drug that selectively modifies platelet function to inhibit thromboxane $A_2$ formation could be of considerable benefit in migraine therapy.

Abnormalities of platelet behaviour have been reported in patients with diabetes mellitus (Metabolism, 1979, 28, 394, Lancet, 1978, (i) 235). Diabetic patients are known to be particularly susceptible to microvascular complications, atherosclerosis and thrombosis and platelet hyper-reactivity has been suggested as the cause of such angiopathy. Diabetic platelets produce elevated amounts of $TxB_2$ and malondialdehyde (Symposium "Diabetes and Thrombosis - Implications for Therapy," Leeds U.K., April 1979). Also it has been shown that in rats with experimental diabetes vascular prostacyclin production is impaired and $TxA_2$ synthesis from the platelets is elevated (IV International Prostaglandin Conference, Washington, D.C. May 1979). Thus the imbalance between prostacyclin and $TxA_2$ is considered to be responsible for the microvascular complications of diabetes. A $TxA_2$-synthetase inhibitor could therefore find clinical utility in preventing these vascular complications.

Aspirin and most other non-steroidal anti-inflammatory drugs inhibit the cyclo-oxygenase enzyme. The effect of this is to shut down the production of the $PGG_2/H_2$ endoperoxides and by so doing to reduce both the prostacyclin and thromboxane $A_2$ levels. Aspirin and aspirin-like drugs have been evaluated clinically for prevention of stroke and heart attack (New England and J. Med. 1978, 299, 53, B.M.J., 1978, 1188, Stroke, 1977, 8, 301).

Although some encouraging results have been obtained with these drugs, a compound which specifically inhibits thromboxane $A_2$ formation leaving the biosynthesis of prostacyclin unimpaired would be more valuable in these clinical conditions (Lancet (ii), 1978, 780).

The ability of primary neoplasms to metastasize is a principal cause of failure to cure human cancers. It has been suggested that metastatic tumour cells can alter the critical $PGI_2$-$TxA_2$ balance in favour of thrombosis (Science, 1981, 212, 1270). Prostacyclin has recently been shown to be a powerful anti-metastatic agent by virtue of its platelet anti-aggregatory action. This result indicates that a $TxA_2$-synthetase inhibor may function as an anti-metastatic agent in vivo (J. Cell. Biol. 1980, 87 64).

U.K. patent application No. 2045244A claims selective thromboxane synthetase inhibitors of the formula:

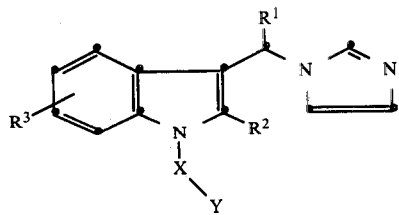

These compounds differ substantially from the present compounds.

A publication in *Eur. J. Med. Chem.—Chimica Theropeutica*, May-June 1975, vol. 10, No. 3, p. 276-285 discloses antiinflammatory antiarthritic and fibrinolytic agents of the formula:

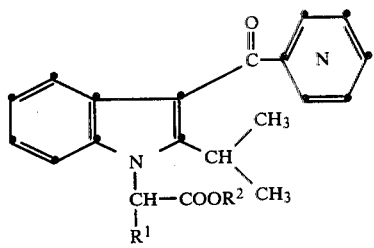

and related compounds.

SUMMARY OF THE INVENTION

This invention relates to indole derivatives, and in particular to certain 3-(pyrid-3- or -4-ylalkyl)indoles. Such compounds are able to selectively inhibit the action of the thromboxane synthetase enzyme without significantly inhibiting the action of the prostacyclin synthetase or cyclo-oxygenase enzymes. The compounds may thus be useful in, for example, the treatment of thrombosis, ischaemic heart disease, stroke, transient ischaemic attack, migraine, cancer and the vascular complications of diabetes.

Thus, according to the invention there are provided compounds of the general formula:

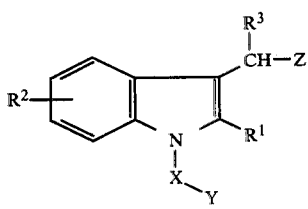

wherein
$R^1$ is hydrogen, $C_1$-$C_4$ alkyl, $C_3$-$C_7$ cycloalkyl or phenyl;
$R^2$ is hydrogen, $C_1$-$C_4$ alkyl, $C_1$-$C_4$ alkoxy, or halo;
$R^3$ is hydrogen or $C_1$-$C_4$ alkyl;
X is —$(CH_2)_n$— where n is 1, 2 or 3,

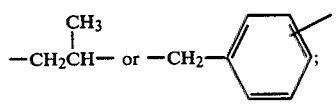

Y is —COOH, —COO($C_1$-$C_4$ alkyl), —CONH$_2$, —CN or 5-tetrazolyl;

and
Z is 3- or 4-pyridyl;
and the pharmaceutically acceptable salts thereof.
"Halo" means F, Cl, Br or I.
Alkyl and alkoxy groups of 3 or 4 carbon atoms may be straight or branched chain.
$R^1$ is preferably $CH_3$.
$R^2$ and $R^3$ are each preferably H or $CH_3$.
X is preferably —$CH_2CH_2$— or —$CH_2CH(CH_3)$—.
Y is preferably —COOH.
Z is preferably 3-pyridyl.
The preferred cycloalkyl group is cyclopropyl.
The preferred individual compounds have the formulae:

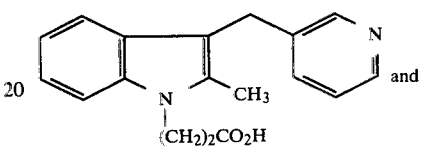

and

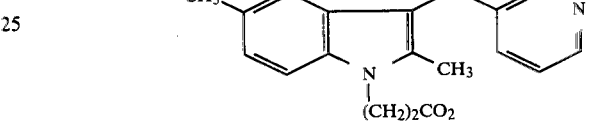

The invention also provides a method of inhibiting the action of the thromboxane synthetase enzyme in an animal, including a human being, without significantly inhibiting the action of the prostacyclin synthetase or cyclo-oxygenase enzymes, which comprises administering to the animal an effective amount of a compound of the formula (I), or a pharmaceutically acceptable salt thereof, or a pharmaceutical composition comprising such a compound or salt together with a pharmaceutically acceptable diluent or carrier.

The invention further provides a compound of the formula (I), or a pharmaceutically acceptable salt thereof, for use in treating an animal, including a human being, to inhibit the action of the thromboxane synthetase enzyme without significantly inhibiting the action of the prostacyclin synthetase or cyclo-oxygenase enzymes.

The invention also includes a pharmaceutical composition comprising a compound of the formula (I), or a pharmaceutically acceptable salt thereof, together with a pharmaceutically acceptable diluent or carrier.

Pharmaceutically acceptable acid addition salts of the compounds of the invention are salts with acids containing pharmaceutically acceptable anions, e.g. the hydrochloride, hydrobromide, sulphate or bisulphate, phosphate or acid phosphate, acetate, maleate, fumarate, lactate, tartrate, citrate, gluconate, succinate and p-toluene sulphonate salts. Compounds in which Y is $CO_2H$ may form pharmaceutically acceptable cationic salts such as sodium, potassium and ammonium salts.

DETAILED DESCRIPTION OF THE INVENTION

The compounds of the formula (I) may be prepared by a number of different routes:
(1) The compounds of the formula (I) may be prepared from a compound of the formula:

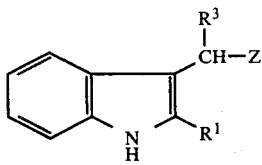

(II)

where $R^1$, $R^2$, $R^3$ and Z are as defined for formula (I), by reacting the anion derived from (II) using a strong base, with an alkylating agent of the formula:

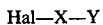

(III)

where Hal is Cl, Br or I and X and Y are as defined for formula (I).

Suitable bases for generating the anion from (II) include sodamide and alkali metal hydrides: sodium hydride is preferred. "Hal" is preferably Br.

In a typical procedure, compound (II) is dissolved in a suitable organic solvent, e.g. dry dimethylformamide (DMF), and sodium hydride is then carefully added. After formation of the anion is complete, the alkylating agent (III) is added in a suitable organic solvent, and the resulting solution stirred at room temperature for up to about 24 hours. If necessary, the reaction mixture can be heated at up to about 130° C. to accelerate the reaction. The product can then be isolated and purified by conventional procedures.

The compounds of the formula (I) may, for example, be prepared by the following procedures:

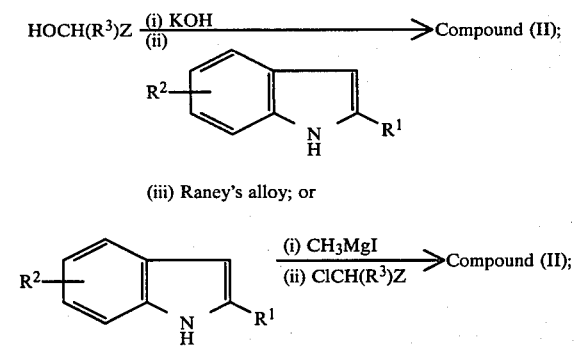

(iii) Raney's alloy; or

Intermediates in which $R^3$ is $C_1$-$C_4$ alkyl can also be prepared by the following route:

the intermediate in which $R^3$ is $CH_3$ yields the compound in which $R^4$ is $CH_2$, which compound is then hydrogenated (using e.g. Pd/C, $C_2H_5OH$, $H_2$ at 2-5 atm.) to the desired end product.

This reaction can be carried out by conventional procedures, such as those described in J. Het. Chem. 9, 833 (1972).

The indole starting materials are described in the specification of European Patent Application No. 3901, published 5th Sept., 1979.

(2) Compounds of the formula (I) where X is —($CH_2$)$_2$— and Y is —CN or —$CO_2$ ($C_1$-$C_4$ alkyl) may be prepared by reaction of a compound of the formula (II) with acrylonitrile or a $C_1$-$C_4$ alkyl ester of acrylic acid, respectively, in the presence of a base. Similarly, compounds where X=—$CH_2CH(CH_3)$— and Y=—CN or —$CO_2$ ($C_1$-$C_4$ alkyl) may be prepared analogously using methacryolnitrile or a $C_1$-$C_4$ alkyl ester of methacrylic acid. The reaction is generally performed with the compound of formula (II) and the acrylic derivative dissolved in a suitable solvent, e.g. dioxan or tetrahydrofuran. A strong organic base e.g. benzyltrimethylammonium hydroxide in methanol ("Triton B"—Trade Mark) is then added and the resulting solution is then either stirred at room temperature, or if necessary, heated at up to reflux temperature, for up to about 6 hours. The product can then be isolated and purified by conventional procedures.

(3) Naturally certain of the groups Y may be obtained by chemical transformation reactions and these possibilities will be well known to those skilled in the art. Thus, for example, compounds of the formula (I) wherein Y is a carboxyl group may be obtained by the alkaline hydrolysis of the corresponding esters where Y is —COO($C_1$-$C_4$ alkyl). The acid may be converted to a variety of derivatives, e.g. formation of the acid chloride or imidazolide followed by reaction with ammonia gives the amides where Y is $CONH_2$, or reaction of the acid with a $C_1$-$C_4$ alkanol in the presence of an acid catalyst gives the $C_1$-$C_4$ alkyl esters.

The amides where Y is $CONH_2$ may also be prepared via hydrolysis of the compound of formula (I) where Y is a cyano group, e.g. using concentrated hydrochloric acid in the case of the alkyl nitriles where X is ($CH_2$)$_n$ or —$CH_2CH(CH_3)$—, or alkaline hydrogen peroxide in the case of the aryl nitriles where X is:

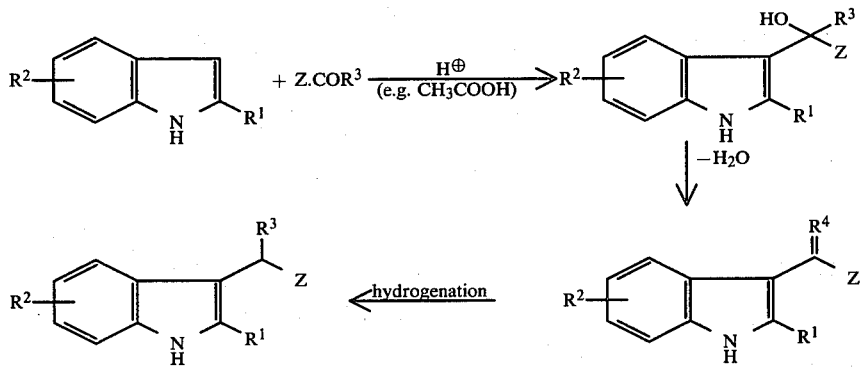

$R^1$, $R^2$, $R^3$ and Z are as defined for formula (I).

$R^4$ is the alkylene group having the same number of carbon atoms as $R^3$. For example, the dehydration of

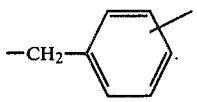

More vigorous alkaline hydrolysis of the nitrile, e.g. using an alkali metal hydroxide and reflux, can also be used to give the corresponding acids where Y is a carboxyl group, or alternatively, the 5-tetrazolyl ring may be built up by reaction of the nitrile with sodium azide and ammonium chloride. Also, the esters in which Y is $-COO(C_1-C_4$ alkyl) can be reacted with ammonia to form the corresponding amides.

All these reactions are entirely conventional and the methods and conditions for their performance will be well known to those skilled in the art, as with other possibilities and variations.

The pharmaceutically acceptable acid addition salts of the compounds of the invention may be prepared by conventional procedures, e.g. by reacting the free base in a suitable solvent, e.g. ethanol, with a solution containing one equivalent of the desired acid in a suitable solvent, e.g. ether. The salt generally precipitates from solution or is recovered by evaporation of the solvent. Similarly the cationic salts can be prepared by conventional procedures.

Where the compound of the invention contains an asymmetric carbon atoms the invention includes the racemic mixtures and the separated D- and L-optically active isomeric forms. Such forms should be obtainable by conventional methods, e.g. by fractional crystallisation of a salt with a suitable optically active acid, e.g. tartaric acid.

The compounds of the formula (I) and their pharmaceutically acceptable salts have been found to selectively inhibit the action of the thromboxane synthetase enzyme without significantly affecting the action of the prostacyclin synthetase of cyclooxygenase enzymes. Thus the compounds are of value in the treatment of a variety of clinical conditions which are characterized by an imbalance of prostacyclin/thromboxane $A_2$. For the reasons given above these conditions may include thrombosis, ischaemic heart disease, stroke, transiet ischaemic attach, migraine, cancer and the vascular complications of diabetes.

The effect of the compounds of the formula (I) on the thromboxane synthetase enzyme, and the prostacyclin synthetase and cyclooxygenase enzymes has been measured by the following in vitro enzyme assays:

1. Cyclo-oxygenase

Ram seminal vesicle microsomes (Biochemistry, 1971, 10, 2372) are incubated with arachidonic acid (100 μM: 1 min.: 22°) to produce $PGH_2$ and aliquots of the reaction mixture injected into a stream of Krebs-bicarbonate at 37° C. (containing a mixture of antagonists (Nature, 1978, 218, 1135) and indomethacin (Brit. J. Pharmacol., 1972, 45 451) which is superfusing a spirally-cut rabbit aorta strip (Nature, 1969, 223, 29).

The ability of a compound to inhibit the enzyme is measured by comparing the increases in isometric tension produced by $PGH_2$ in the absence of the test compound, and following pre-incubation of the enzyme with the test compound for 5 minutes.

2. Prostacyclin ($PGI_2$) Synthetase

Pig aorta microsomes (Nature, 1976, 263, 663) are incubated (30 sec.: 22° C.) with $PGH_2$ produced as in 1) and aliquots bio-assayed as in 1. $PGI_2$ production is assessed indirectly by measuring the decrease in $PGH_2$-induced tension ($PGI_2$ itself does not contract the aorta). This decrease can be prevented completely by pre-incubation of the enzyme with the selective $PGI_2$ synthetase inhibitor, 15-hydroxy-arachidonic acid (Prostaglandins, 1976, 12, 715). The test compound is then pre-incubated with the enzyme for 5 minutes, and its ability to prevent the decrease in tension is measured.

3. Thromboxane $A_2$ ($TxA_2$) Synthetase

Indomethacin pre-treated human platelet microsomes (Science, 1976, 193, 163) are incubated (2 min.: 0° C.) with $PGH_2$ (produced as in 1) and aliquots of the reaction mixture superfused over two rabbit aorta spirals which are separated by a delay coil (2 min.). The latter is required to allow the selective decay of the more unstable thromboxane $A_2$ (Proc. Nat. Acad. Sci., 1975, 72, 2994) thereby enabling the separate measurement of increased isometric tension due to the $TxA_2$ formed and the $PGH_2$ remaining. The test compound is pre-incubated with enzyme for 5 minutes, and its ability to inhibit the thromboxane synthetase enzyme is measured as its reduction of the $TxA_2$ component of the isometric tension.

Compounds of the invention tested in this way have been shown to be capable of selectively inhibiting the thromboxane synthetase enzyme.

In addition to the above an *in vitro* assay for measuring the inhibition of human blood platelet aggregation has been described and this may be predictive of anti-thrombotic efficacy clinically (Lancet (ii), 1974, 1223, J. Exp. Med., 1967, 126, 171). Both clinically effective agents aspirin and sulphinpyrazone show inhibitory activity *in vitro* against a variety of aggregating agents in this test.

A number of *in vivo* tests in animals have also been described for evaluating potential anti-thrombotic drugs.

The method of Patrono et al is adapted to study the generation of $TxB_2$ in whole blood samples removed from animals prior to and following drug treatment. Briefly, blood samples are taken into glass tubes and allowed to clot at 37° C. Serum is separated by centrifugation and the samples stored at −40° C. until assayed for $TxB_2$, when appropriate dilutions of ethanol deproteinised samples are analysed by RIA. This technique is used in experiments with the test compounds to determine intravenous potency in anaesthetised rabbits:

Anaesthetised Rabbits

Male New Zealand white rabbits (2.6–5.6 kg) are anaesthetised with sodium pentobarbitone (30 mg/kg i.v.) followed by urethane (500 mg/kg i.p.). After cannulation of the trachea, a carotid artery is catheterised for collection of blood samples. The catheter is kept patent by slow infusion (0.2 ml/minute) of sterile saline. Control carotid arterial blood samples are taken 30 and 5 minutes prior to administration of the test compound or vehicle (0.9% w/v NaCl, 0.2 ml/kg) via a marginal ear vein. Three groups of rabbits are used. The first group receive 0.03 mg/kg of the test compound followed, one hour later, by 0.1 mg/kg. Similarly, the second group receive 0.3 mg/kg, followed by 1 mg/kg. The third group receive vehicle, followed one hour later by a further vehicle injection. Carotid arterial blood samples are taken 15 and 45 minutes after all doses. At each time point, a 1 ml blood sample is taken into a glass test tube, without anticoagulant, for $TxB_2$ determination. For the latter, the blood sample is allowed to clot during a two hour incubation at 37° C. (which preliminary experiments had shown to give maximum TxB$_2$ production) and the serum obtained by centrifugation. Serum samples are then processed through the TxB$_2$ RIA after deproteinisation with ethanol and dilution with Isogel Tris buffer.

Intravenous injection of arachidonic acid causes death in rabbits by causing platelet clumping and embolisation in the lungs. Again both the clinically effective aspirin (Agents and Actions, 1977, 1, 481) and sulphinpyrazone (Pharmacology, 1976, 14, 522) protect the rabbit from the lethal effect of the injection. Sulphinpyrazone has also been shown to prevent the aggregation of platelets in an extra corporeal loop of the abdominal aorta of rats in vivo (Thromb. Diathes. Haem., 1973, 30, 138).

The compounds may be administered orally in the form of tablets or capsules containing a unit dose of the compound together with such excipients as maize starch, calcium carbonate, dicalcium phosphate, alginic acid, lactose, magnesium stearate, "Primogel" (Trade Mark) or talc. The tablets are typically prepared by granulating the ingredients together and compressing the resulting mixture to give tablets of the desired size. Capsules are typically prepared by granulating the ingredients together and filling them into hard gelatine capsules of the appropriate size to contain the desired dosage.

The compounds may also be administered parenterally, for example by intramuscular, intravenous or subcutaneous injection. For parenteral administration, they are best used in the form of a sterile aqueous solution which may contain other solutes such as tonic and pH adjusters. The compounds may be added to distilled water and the pH adjusted to 3-6 using an acid such as citric, lactic or hydrochloric acid. Sufficient solutes such as dextrose or saline may be added to render the solution isotonic. The resulting solution may then be sterilised and filled into sterile glass vials of an appropriate size to contain the desired volume of solution. The compounds of the invention may also be administered by the infusion of a parenteral formulation as described above into a vein.

For oral administration to human patients, it is expected that the daily dosage level of a compound of the formula (I) will be from 0.1 to 20 mg/kg per day for a typical adult patient (70 kg). For parenteral administration, it is expected that the daily dosage level of a compound of the formula (I) will be from 0.01-0.5 mg/kg. per day, for a typical adult patient. Thus tablets or capsules can generally be expected to contain from 5 to 150 mg of the active compound for administration orally up to 3 times a day. Dosage units for parenteral administration can be expected to contain from 0.5-35 mg of the active compound. A typical vial could be a 10 ml vial containing 5 mg of the active compound in 6-10 ml of solution.

It should of course be appreciated that in any event the physician will determine the actual dosage which will be most suitable for the individual and it will vary with the age, weight and response of the patient.

The above dosages are exemplary of the average patient, there may of course be individual cases where higher or lower dosage ranges are merited.

Compounds of the formula (II) tested using the methods previously described have been shown to be capable of selectively inhibiting the thromboxane synthetase enzyme.

The preparation of the novel compounds of the formula (I) is illustrated by the following Examples:

EXAMPLE 1

Preparation of:
(A) Ethyl 2-[2-Methyl-3-(3-Pyridylmethyl)indol-1-yl]acetate
(B) 2-[2-Methyl-3-(3-Pyridylmethyl)indol-1-yl]acetic acid ¼ hydrate

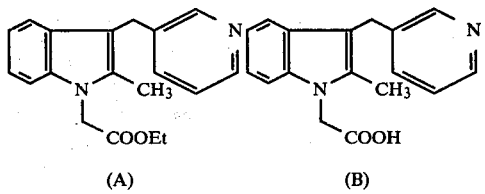

(A)        (B)

(A) Sodium hydride (50% dispersion in oil) (0.53 g) was added portionwise to a solution of 2-methyl-3-(3-pyridylmethyl)indole (2.22 g) in dry DMF (50 ml) at 20° and the resulting mixture stirred at room temperature (20°) for 1½ hours. A solution of ethyl bromoacetate (1.8 g) in dry DMF (25 ml) was then added dropwise and the resulting solution stirred at room temperature overnight. The solvent was then removed under reduced pressure and the residual oil dissolved in hot toluene, cooled, and the solid filtered off. The toluene filtrate was evaporated and the residual oil chromatographed (silica gel, eluting with 10% 40°-60° pet. ether in CH$_2$Cl$_2$). The product was then crystallized from toluene to yield the title ester, 1.4 g, mp 84°-86°.

Analysis %: Found: C, 79.0; H, 6.5; N, 8.9. Calculated for C$_{19}$H$_{20}$N$_2$O$_2$: C, 79.0; H, 6.55; N, 8.9.

(B) The ester from (A) (1.0 g) was added to a solution of KOH (0.3 g) in H$_2$O (10 ml) and the resulting solution heated on a steam bath for 4 hours. After cooling the solution was acidified with acetic acid and the solid filtered off and recrystallized from isopropylalcohol to yield the title acid, 0.4 g, m.p. 223°-225°.

Analysis %: Found: C, 71.9; H, 5.9; N, 9.4. Calculated for C$_{17}$H$_{16}$N$_2$O$_2$.¼H$_2$O: C, 71.7; H, 5.8; N, 9.8.

EXAMPLE 2

Preparation of:
1-(2-Cyanoethyl)-2-methyl-3-(3-pyridylmethyl)indole

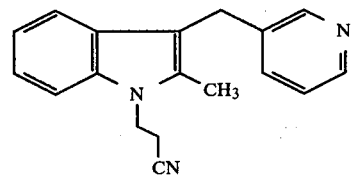

2-Methyl-3-(3-pyridylmethyl)indole (3.2 g) was dissolved in dioxan (50 ml) and stirred at room temperature during the dropwise addition of "Triton B" (Trade Mark) in methanol (1 ml) and acrylonitrile (0.84 g). The solution was stirred at room temperature for 2 hours before removal of the solvent and addition of H$_2$O (25 ml) to the residue. The aqueous solution was then extracted with CH$_2$Cl$_2$ (3×25 ml) and the combined organic extracts washed with saturated aqueous NaCl solution, dried (MgSO$_4$), filtered and evaporated to give an oil. The oil was chromatographed (silica gel: elutant 10% 60°–80° pet. ether in $CH_2Cl_2$) and the product recrystallized from toluene to yield the title compound, 1.2 g, m.p. 122°.

Analysis %: Found: C, 78.45; H, 6.25; N, 15.5%. Calculated for $C_{18}H_{17}N_3$: C, 78.45; H, 6.2; N, 15.25%.

EXAMPLES 4–7

Compounds of the invention prepared by the treatment of a pyridylalkylindole with acrylonitrile or methacrylonitrile by a procedure similar to that of Example 2, followed by hydrolysis of the resulting nitrile according to the method of Example 3, are listed in Table 1:

TABLE 1

| Example No. | Compound | M.P. °C. | Analysis % |
|---|---|---|---|
| 4 | 1-(2-carboxyethyl)-5-methyl-2-methyl-3-(3-pyridylmethyl)indole | 209–210 | Found: C,73.65; H,6.53; N,9.08. $C_{19}H_{20}N_2O_2$ Requires: C,74.00; H,6.54; N,9.09% |
| 5 | 1-(2-carboxyethyl)-5-chloro-2-methyl-3-(3-pyridylmethyl)indole | 197–198 | Found: C,65.79; H,5.30; N,8.58. $C_{18}H_{17}ClN_2O_2$ Requires: C,65.75; H,5.21; N,8.52% |
| 6 | 1-(2-carboxyethyl)-2-methyl-3-(1-(3-pyridyl)ethyl)indole | | Found: C,73.98; H,6.55; N,9.13. $C_{19}H_{20}N_2O_2$ Requires: C,74.00; H,6.54; N,9.09% |
| 7 | 1-(2-carboxypropyl)-2-methyl-3-(3-pyridylmethyl)indole | 164–166 | Found: C,73.58; H,6.54; N,8.84. $C_{19}H_{20}N_2O_2$ Requires: C,74.00; H,6.54; N,9.09% |

EXAMPLE 3

Preparation of: 1-(2-Carboxyethyl)-2-methyl-3-(3-pyridylmethyl)indole

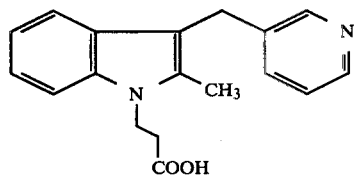

The nitrile from Example 2 (0.9 g) was added to a 10% aqueous ethanolic KOH solution (8 ml) and heated under reflux for 5 hours. The solution was then just acidified with acetic acid and evaporated. Water was added and the resulting solid was filtered off and recrystallized from aqueous EtOH to yield the title compound, 0.3 g, m.p. 180°–181°.

Analysis %: Found: C, 72.9; H, 6.2; N, 9.6 Calculated for $C_{18}H_{18}N_2O_2$: C, 73.45; H, 6.15; N, 9.5.

EXAMPLE 8

1-(2-Carbomethoxyethyl)-2-cyclopropyl-3-(3-pyridylmethyl)indole

A mixture of 2-cyclopropyl-3-(3-pyridylmethyl)indole (1.98 g), methacrylate (2.06 g) and "Triton B" in methanol (0.5 ml) in tetrahydrofuran (50 ml) was heated under reflux for 4 hours and then evaporated. The residue was dissolved in ethyl acetate and the solution was washed with water and dried ($Na_2SO_4$). Evaporation of the solvent gave an oil which was chromatographed on silica gel. Elution with a mixture of chloroform and petrol (b.p. 40°–60°) (3:1) gave 1-(2-carbomethoxyethyl)-2-cyclopropyl-3-(3-pyridylmethyl)indole as an oil (1.20 g).

Analysis %: Found: C,74.82; H,6.63; N,8.14. $C_{21}H_{22}N_2O_2$ Requires: C,75.42; H,6.63; N,8.38.

EXAMPLE 9

1-(2-Carboxyethyl)-2-cyclopropyl-3-(3-pyridylmethyl)indole

A mixture of 1-(2-carbomethoxyethyl)-2-cyclopropyl-3-(3-pyridylmethyl)indole (1.0 g), sodium hydroxide (0.18 g), methanol (1 ml) and water (10 ml) was heated under reflux for six hours. The resulting solution was evaporated to dryness and the residue was dissolved in a small volume of water. Acidification with acetic acid gave a solid which was filtered off, washed with water, dried and crystallised from isopropanol/petrol (b.p. 60°–80°) to give 1-(2-carboxyethyl)-2-cyclopropyl-3-(3-pyridylmethyl)indole (0.55 g), m.p. 159°–160°.

Analysis %: Found: C,75.21; H,6.38; N,8.44. $C_{20}H_{20}N_2O_2$ Requires: C,74.97; H,6.29; N,8.74.

EXAMPLES 10–12

Compounds of this invention prepared by treatment of a pyridylmethylindole with methyl acrylate by a procedure similar to that of Example 8, followed by hydrolysis of the resulting ester according to the method of Example 9, are listed in Table 2:

Analysis %: Found: C,73.46; H,6.58; N,14.05. $C_{18}H_{19}N_3O$ Requires: C,73.69; H,6.53; N,14.32.

EXAMPLE 14

1-[2-(5-Tetrazolyl)ethyl]-2-methyl-3-(3-pyridylmethyl)indole

A mixture of 1-(2-cyanoethyl)-2-methyl-3-(3-pyridylmethyl)indole (0.8 g), sodium azide (0.95 g), ammonium chloride (0.78 g) and dry dimethylformamide (12 ml) was heated with stirring at 125° C. for 20 hours and then evaporated. Water (25 ml) was added to the residue to dissolve inorganic material. The insoluble portion was crystallised from methanol/ethyl acetate to give 1-[2-(5-tetrazolyl)ethyl]-2-methyl-3-(3-pyridylmethyl)indole (0.20 g), m.p. 173°.

Analysis %: Found: C,67.45; H,5.79; N,27.06. $C_{18}H_{18}N_6$ Requires: C,67.90; H,5.70; N,26.40.

EXAMPLE 15

1-(4-Carbethoxybenzyl)-2-methyl-3-(3-pyridylmethyl)indole hydrochloride

Sodium hydride (0.24 g of 50% dispersion in mineral oil) was added portionwise to a stirred solution of 2-methyl-3-(3-pyridylmethyl)indole (1.0 g) in dry dimeth-

TABLE 2

| Example No. | Compound | M.P. °C. | Analysis % |
|---|---|---|---|
| 10 | 2-CH₃, 1-(CH₂CH₂CO₂H), 3-(3-pyridylmethyl)indole | 194–195 | Found: C,73.27; H,6.37; N,9.42. $C_{18}H_{18}N_2O_2$ Requires: C,73.45; H,6.16; N,9.52% |
| 11 | 2-C₆H₅, 1-(CH₂CH₂CO₂H), 3-(3-pyridylmethyl)indole | 194–195 | Found: C,77.18; H,5.72; N,8.02. $C_{23}H_{20}N_2O_2$ Requires: C,77.50; H,5.66; H.7.86% |
| 12 | 5-CH₃O, 2-CH₃, 1-(CH₂CH₂CO₂H), 3-(3-pyridylmethyl)indole | 181–183 | Found: C,70.60; H,6.40; N,8.47. $C_{19}H_{20}N_2O_2$ Requires: C,70.35; H,6.22; N,8.64% |

EXAMPLE 13

1-(2-Carbamoylethyl)-2-methyl-3-(3-pyridylmethyl)indole 1-(2-Cyanoethyl)-2-methyl-3-(3-pyridylmethyl)indole (1.0 g) was dissolved in concentrated hydrochloric acid (10 ml) and the solution was allowed to stand at room temperature for 24 hours. The solution was cautiously basified by addition of dilute KOH solution with cooling to give an oil which gradually solidified. The solid was filtered off, washed with water and crystallised from isopropanol/water to give 1-carbamoylethyl)-2-methyl-3-(3-pyridylmethyl)indole (0.44 g), m.p. 145°147°.

ylformamide (15 ml) and the mixture was stirred for 30 minutes. Ethyl 4-bromomethylbenzoate (1.10 g) was then added and the mixture was stirred at room temperature for 2.5 hours and then evaporated. The residue was dissolved in ethyl acetate and the solution was washed well with water and dried ($Na_2SO_4$). Evaporation of the solvent gave an oil which was chromatographed on silica gel. Elution with chloroform first give mineral oil followed by pure product as an oil (1.3 g).

A portion of the oil was dissolved in a small volume of ether and an excess of an ethereal solution of hydrogen chloride was added. The solid was filtered off and crystallised from methanol/ethyl acetate to give 1-(4-carbethoxybenzyl)-2-methyl-3-(3-pyridylmethyl)indole hydrochloride, m.p. 176°–179° C.

Analysis %: Found: C,71.09; H,6.06; N,6.68. C$_{25}$H$_{24}$N$_2$O$_2$, Requires: C,71.33; H,5.99; N,6.65.

The following illustrates the preparation of certain starting materials used in the previous Examples. All temperatures are in °C.:

PREPARATION 1

Preparation of 2-Methyl-3-(3-pyridylmethyl)indole

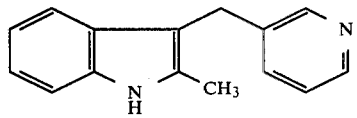

3-Pyridylmethanol (27.25 g) was added to a suspension of KOH (2.24 g) in xylene (200 ml), and the mixture heated at reflux using a Dean and Stark apparatus to remove the water. After cooling, 2-methylindole (16.4 g) was added and the mixture heated at reflux for 3 hours. "Raneys Alloy" (1.0 g) was then added to the hot solution and heating at reflux was continued overnight. After cooling, the metallic residue was filtered off and washed with ether (25 ml). The combined organic filtrate was extracted with H$_2$O (2×100 ml) and the organic layer separated and cooled to 0° C., whereupon a solid precipitated which was filtered off. Crystallization of the solid from toluene afforded the pure title compound, 14.6 g, m.p. 207°–210°.

Analysis %: Found: C,81.05; H,6.35; N,12.6%. Calculated for C$_{15}$H$_{14}$N$_2$: C,80.6; H,6.3; N,12.15%.

PREPARATION 2

2-Methyl-3-(4-pyridylmethyl)indole

Methyl iodide (32.0 g) in dry ether (100 ml) was added dropwise to a stirred mixture of magnesium and dry ether (50 ml) at such a rate that the reaction was not too vigorous. After completion of the addition the mixture was heated under reflux for 30 minutes and then cooled to 0°. A solution of 2-methylindole (16.9 g) in dry ether (100 ml) was added dropwise with stirring and the resulting mixture was then heated under reflux for 1.5 hours. It was then cooled to 0° and 4-chloromethyl pyridine hydrochloride (10.5 g) was added portionwise with stirring. The mixture was heated under reflux with stirring for 3 hours and then cooled. A solution of ammonium chloride (30 g) in water (200 ml) was added dropwise with stirring and then the layers were separated. The ether layer was dried (Na$_2$SO$_4$) and evaporated to give an oil which was chromatographed on silica gel. Elution with chloroform initially gave some impurity together with the starting indole. Further elution gave 2-methyl-3-(4-pyridylmethyl)indole (8.0 g), m.p. 126°–127° C. (from ether).

Analysis %: Found: C,81.32; H,6.39; N,12.45. C$_{15}$H$_{14}$N$_2$. Requires: C,81.05; H,6.35; N,12.60.

Other starting materials prepared in the same way using 3-chloromethylpyridine hydrochloride and the appropriate indole are listed in Table A:

| Compound | M.P. °C. | Analysis % |
|---|---|---|
| [structure: indole with cyclopropyl-N substituent on pyridyl] | 188–189 | Found: C,81.73; H,6.54; N,11.07. C$_{17}$H$_{16}$N$_2$ Requires: C,82.22; H,6.50; N,11.28% |
| [structure: indole with C$_6$H$_5$ and pyridyl] | 184–185 | Found: C,84.59; H,5.56; N,9.69. C$_{20}$H$_{16}$N$_2$$^a$ Requires: C,84.48; H,5.67; N,9.85% |
| [structure: 5-methylindole with CH$_3$ and pyridylmethyl] | 168–171 | Found: C,81.20; H,6.87; N,11.45. C$_{16}$H$_{16}$N$_2$ Requires: C,81.32; H,6.83; N,11.86% |
| [structure: 5-chloroindole with CH$_3$ and pyridylmethyl] | 171–173 | Found: C,70.29; H,5.14; N,10.59. C$_{15}$H$_{13}$ClN$_2$$^a$ Requires: C,70.17; H,5.11; N,10.9% |
| [structure: 5-methoxyindole with CH$_3$ and pyridylmethyl] | | This intermediate was partially purified and then used directly without characterisation. |

$^a$STARTING INDOLE DISSOLVED IN DRY TETRAHYDROFURAN

PREPARATION 3

2-Methyl-3(1-[3-pyridyl]ethyl)indole

A solution of 1-(2-methyl-3-indolyl)-1-(3-pyridyl-)ethylene (prepared according to J. Het. Chem., 9, 833, 1972) (9.37 g) in ethanol (200 ml) was hydrogenated at 2.5 atm. pressure in the presence of 10% palladium/-charcoal. The solution was filtered and evaporated and the residue was crystallised from ethyl acetate/petrol (b.p. 60°–80°) to give 2-methyl-3[1-(3-pyridyl)ethyl]indole (5.74 g) m.p. 139°–141° C.

Analysis %: Found: C,81.56; H,7.11; N,11.65. $C_{16}H_{16}N_2$. Requires: C,81.32; H,6.83; N,11.86%.

We claim:

1. Compounds of the formula:

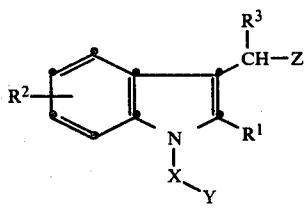

where
R$^1$ is hydrogen, $C_1$–$C_4$ alkyl, $C_3$–$C_7$ cycloalkyl or phenyl;
R$^2$ is hydrogen, $C_1$–$C_4$ alkyl, $C_1$–$C_4$ alkoxy, or halo;
R$^3$ is hydrogen or $C_1$–$C_4$ alkyl;
X is —(CH$_2$)$_n$— where n is 1, 2 or 3, —CH$_2$CH(CH$_3$)— or

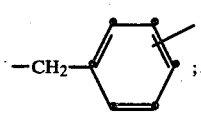

Y is —COOH, —COO ($C_1$–$C_4$ alkyl), —CONH$_2$, —CN or 5-tetrazolyl;
and Z is 3- or 4-pyridyl;
and the pharmaceutically acceptable salts thereof.

2. A compound as claimed in claim 1 in which R$^1$ is CH$_3$.

3. A compound as claimed in claim 1 or 2 in which R$^2$ and R$^3$ are each H or CH$_3$.

4. A compound as claimed in claim 1 in which X is —CH$_2$CH$_2$— or —CH$_2$CH(CH$_3$)—.

5. A compound as claimed in claim 1 in which Y is —COOH.

6. A compound as claimed in claim 1 in which Z is 3-pyridyl.

7. A compound of the formula:

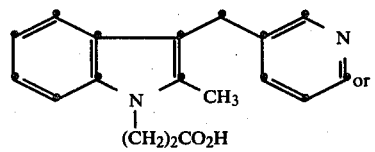 or

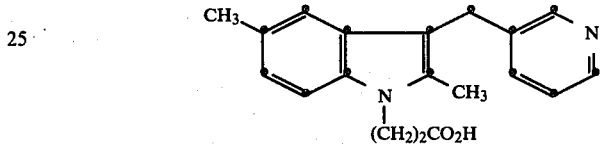

* * * * *